US005665414A

United States Patent [19]
Sherwood et al.

[11] Patent Number: 5,665,414
[45] Date of Patent: Sep. 9, 1997

[54] CELLULOSIC MATERIALS FOR INCORPORATION INTO FOOD PRODUCTS AND METHODS OF MAKING SAME

[75] Inventors: Bob E. Sherwood, Amenia, N.Y.; Jouko Johannes Virtanen, Marion, Iowa

[73] Assignee: Edward Mendell Co., Inc., Patterson, N.Y.

[21] Appl. No.: 419,633

[22] Filed: Apr. 6, 1995

[51] Int. Cl.⁶ .......................... A23C 19/09; A23L 1/0534
[52] U.S. Cl. .......................... 426/582; 426/262; 426/573; 426/615; 426/804
[58] Field of Search .............................. 426/582, 615, 426/804, 262, 573

[56] References Cited

U.S. PATENT DOCUMENTS

| | | |
|---|---|---|
| 3,141,875 | 7/1964 | Battista. |
| 3,539,365 | 11/1970 | Durand et al.. |
| 4,159,345 | 6/1979 | Takeo et al.. |
| 4,263,344 | 4/1981 | Radvan et al.. |
| 4,311,717 | 1/1982 | McGinley. |
| 4,744,987 | 5/1988 | Mehra et al.. |
| 4,960,605 | 10/1990 | Trecker et al.. |
| 5,011,701 | 4/1991 | Baer et al.. |
| 5,069,919 | 12/1991 | Weibel ................................ 426/804 |
| 5,213,836 | 5/1993 | McGillivray ....................... 426/804 |
| 5,275,833 | 1/1994 | Schmidt ............................ 426/804 |

FOREIGN PATENT DOCUMENTS

| | | |
|---|---|---|
| 0609976 | 8/1994 | European Pat. Off.. |
| 9014017 | 11/1990 | WIPO. |
| 9201390 | 2/1992 | WIPO. |

*Primary Examiner*—Helen Pratt
*Attorney, Agent, or Firm*—Steinberg, Raskin & Davidson, P.C.

[57] ABSTRACT

New cellulosic materials derive from pulps having an ISO brightness of from 80 to about 90 are disclosed. The celluloses substantially match the color of the food products admixed therewith to provide food products such as sauces, emulsions, frozen desserts, reduced fat products and the like with substantially uniform color. The invention also includes substantially non-agglomerating particulate cheese products such as grated or shredded cheeses in admixture with cellulose derived from a pulp having the ISO qualities described above. The cellulose is present in an amount which is sufficient to substantially prevent agglomeration of the particulate cheese product yet is sensorially undetected. Other aspects of the invention include methods of preparing the liquid, semi-solid or frozen food products containing the selected cellulose as well as methods of preparing the substantially non-agglomerating cheese product.

18 Claims, No Drawings

CELLULOSIC MATERIALS FOR INCORPORATION INTO FOOD PRODUCTS AND METHODS OF MAKING SAME

The present invention is directed to the use of celluloses derived from pulps having a color which substantially approximates that of the foods. More particularly, the present invention is directed to food products containing cellulose derivatives which do not detract from the visual or organoleptic qualities of the final food product such as sauces, dressings, cheeses and the like.

BACKGROUND OF THE INVENTION

Food products such as sauces, dressings, processed foods and the like have been known to include microcrystalline cellulose (MCC) or powdered cellulose as an adjunct. One of the chief drawbacks associated with including such celluloses in foods has been the fact that its bright white appearance is often difficult to mask. Thus, consumer acceptance of such food products has been rather low since the products have a specked or mottled appearance. Furthermore, MCC-containing foods often require additional amounts of food colorings to mask the presence of the cellulose. For example, although grated and shredded cheese products are enhanced by the addition of MCC due to its anti-caking properties, such products have not met with commercial success because of the contrast in color between the cheese and MCC.

Grated and shredded cheeses and cheese products have become widely accepted and used by consumers. Typically, grated cheeses are sold in containers which allow them to flow readily and maintain their moisture content and flavor.

One of the chief problems associated with grated cheeses is that the cheese particles are prone to clumping together, causing caking or agglomerating, particularly after refrigeration. Dispensing of the grated cheese from sieve-top containers, therefore, becomes difficult and a source of consumer frustration. For example, in the case of fully cured, grated Parmesan cheese which has a relatively low moisture content (e.g., 12–18%), there is little problem of clumping or agglomeration of the grated cheese product. However, in cases where the grated cheese contains higher levels of moisture and/or oils, agglomeration becomes more of a concern.

Substantial effort has been undertaken over the years to address this problem. For example, one proposed solution is found in U.S. Pat. No. 4,960,605, wherein Parmesan cheese having a moisture level of 30–32% and a fat level of 28–32% is grated and dried to a moisture content of 19–24% by weight and disodium phosphate is blended with the grated cheese either before or after the drying step.

The United States Food and Drag Administration (FDA) has provided guidelines concerning what ingredients can be included with grated cheeses.

In the field of anti-caking agents, the FDA allows manufacturers and distributors to include silicon dioxide, calcium silicate, sodium silico aluminate, microcrystalline cellulose, or any combination of two or more of these anti-caking agents, among others.

An anti-caking agent is often included with shredded cheeses as well in order to prevent agglomeration of the shredded cheese. Shredded cheeses and cheese products are commercially available in the U.S., typically in resealable clear plastic containers. Such shredded cheeses are typically used as toppings for, e.g., homemade Italian and Mexican dishes, such as pizzas, nachos, etc. Examples of commercially available shredded cheeses include be, e.g., mozzarella, Parmesan, romano, cheddar, Monterey Jack, etc. The color of these shredded cheeses differs depending on the particular cheese flavor. Typically, shredded cheeses have a yellow or orange-yellowish color. Microcrystalline cellulose and/or powdered cellulose are often used in these products as an anti-caking agent. Unfortunately, the available forms of such anti-caking agents appear as a white particulate and thus appear as white flecks dispersed in off-white or yellowish shredded cheeses. The anti-caking agent is misidentified as mold by the consuming public and, therefore, the cheese product is not purchased because it is thought to be "spoiled".

Although the above-mentioned agents are known and have been used in a variety of cheese products available to U.S. consumers, the industry still recognizes a need for improved anti-caking agents, both with respect to anti-caking properties and aesthetic properties of the same.

Often, the anti-caking agent is visible in the cheese product to the naked eye. In the case of a cheese which naturally has a yellow or orange-yellowish color, the presence of anti-caking agents which have a different color provide the cheese product with an untoward appearance.

Microcrystalline cellulose has also been proposed as a fat mimetic. For example, PCT publication WO90/14017 discloses a low calorie fat-like aggregate material prepared by spray-drying an aqueous medium containing a mixture of microcrystalline cellulose and a galactomannam gum such as guar gum and optionally, additional materials such as lipophilic or hydrophilic ingredients. The composition is added as a colloid or as an aqueous dispersion to various foods such as salad dressings, frozen food products or dairy products as a fat substitute having a fat-like mouthfeel.

As mentioned above, the color of the microcrystalline cellulose available to food processors is typically a bright white. Thus, even liquid, semi-solid or frozen food products containing MCC can have less than desirable appearance qualities. It would be highly desirable to provide a low cost cellulose-based additive which achieves the same fat mimetic effects.

Because celluloses are useful food adjuncts which have been accepted for use by the FDA, there is a need to address the shortcomings associated with the physical appearance of celluloses when used with food products. The present invention addresses this need.

SUMMARY OF THE INVENTION

It is an object of the present invention to provide cellulose-containing food products having improved visual and organoleptic qualities.

It is a further object of the invention to provide food products containing celluloses which have a substantially identical appearance in color to the food it is incorporated with.

It is another object of the invention to provide non-agglomerating particulate cheese products containing celluloses which have a substantially identical appearance in color to the particulate cheese included therein.

It is a further object of the invention to provide methods of preparing the above-described food products.

It is another object of the invention to accomplish the above objects without the use of dyes to color the cellulose.

A still further object of the invention is to provide lower cost cellulose-based fat mimetic and food products containing the same.

In accordance with the above objects and others which will be apparent to those skilled in the art, the present invention is directed to food products containing cellulose derived from a pulp or pulp blend having an ISO brightness of from about 80 to about 90; preferably from about 83 to about 89 and most preferably from about 85 to about 88. The cellulose is selected so that it substantially resembles the color of the food product and thus can be blended therewith in a manner which allows the final product to be uniform in color and provide a pleasing visual appearance to the consumer. A non-limiting list of food products included in this aspect of the invention includes sauces, dressings, semi-solid foods, emulsion-based food products, frozen desserts, fat-free and/or reduced fat food products. The amount of cellulose included in the food products ranges from about 0.025 to about 4%, preferably from about 0.05 to about 2.5% by weight.

In a further aspect of the invention there are provided substantially non-agglomerating agglomerating cheese products which contain a particulate, i.e. grated or shredded, cheese or cheese-like ingredient in combination with cellulose derived from a pulp having an ISO brightness of from about 80 to about 95; preferably from about 83 to about 89 and most preferably from about 85 to about 88. The cellulose is selected so that it substantially resembles the color of the cheese and is present in the final product in an amount which is sufficient to substantially prevent agglomeration of the particulate cheese. In this regard, the cellulose will be present in amounts ranging from about 0.01 to about 5%; preferably from about 0.05 to about 2%; and most preferably from about 0.1 to about 1.5% by weight of the cheese.

In still further aspects of the invention, methods of preparing the food products and particulate cheese products described above are provided. In the case of food products, the methods include blending a cellulose derived from a pulp having the ISO characteristics described above with one or more food ingredients until a homogeneous blend is obtained. The cellulose can be added to the food products in the form of an aqueous dispersion, powder or particulate. Alternatively, in the case of substantially non-agglomerating food products such as grated or shredded cheeses, the method includes blending a particulate cheese with cellulose derived from a pulp having the visual characteristic and ISO brightness described above. The cellulose is combined with the particulate cheese preferably by mixing the ingredients in a ratio which is sufficient to substantially prevent agglomeration of the particulate cheese without detracting from the taste or visual appeal of the final product.

Furthermore, methods of matching the color of a cellulose with that of a food product such as a cheese are also provided wherein two or more pulps having different ISO brightness values are blended to form a blended pulp product which has an ISO brightness which substantially matches that color of the food product is rendered into cellulose. The cellulose is then combined with the food ingredients as described above.

As a result of the present invention, improved cellulose-containing food products are provided. In the case of sauces, semi-solid and emulsion-based foods, the color-matched celluloses allow the artisan to provide uniform-appearing final products, if desired, without relying upon substantial amounts of colorants. This is especially important in those aspects of the invention were celluloses are used in the food products as fat substitutes since visual appeal of the products will be maximized. In the case of or in semi-solid or emulsion based foods, the cellulose products of the present invention avoid the off-white color typically found when currently available bright white MCC is added. Furthermore, in the case of grated and/or shredded food products such as cheeses, not only are the visual qualities of the cheeses heightened due to the uniformity of color, the products are substantially free of agglomeration and flow readily from shaker containers customarily used by consumers. Improved shredded cheese products are also obtained which are substantially free of agglomeration and which can be removed from storage containers (e.g. plastic resealable envelopes) and spread onto a food. Thus, the present invention also successfully addresses one of the major disadvantages associated with the use of celluloses as an adjunct with grated cheeses.

An additional benefit of the present invention is the fact that the cellulose products of the present invention offer significant cost advantages over the MCC currently used in the food industry. For example, the cellulose products of the present invention provide the fat-mimetic and anti-caking effects that MCC is known to provide but does so at a cost which is substantially lower than currently available MCC. This is primarily due to the fact that the inventive celluloses can be derived from cheaper pulps which have an ISO brightness which is below that found in the pulps currently used for making MCC.

A still further benefit of the present invention is that the celluloses and pulp products of the present invention can be included in pharmaceuticals such as tablets, powders, sachets and the like as a lower cost and environmentally advantageous alternative to the celluloses currently used. For example, MCC is substantially more expensive and can include chlorine-based bleaches to enhance whiteness.

The term "cheese products" is defined for purposes of the present invention as encompassing 100% natural cheeses as well as processed cheese products, cheese substitutes, synthetic cheese products, low fat, dietetic cheeses, or processed cheeses, including low-fat processed cheese products having, e.g., fat-mimetic properties and/or ingredients. Such cheeses may be of any flavor known to those skilled in the art. The term "grated", used in conjunction with cheese products described herein, is defined for purposes of the invention as encompassing any particulate cheese products, and in particular encompasses any comminuted cheese products used in the industry. Grated cheese particles generally will have a nominal diameter from about 0.1 mm to about 3 mm, and more preferably from about 0.5 mm to about 1.7 mm.

The term "shredded" used in conjunction with cheese products described herein is defined for purposes of the present invention as cheese fragments or shreds of about an inch in length. For purposes of the present invention, shredded cheeses shall be understood to be within the scope of the non-agglomerating cheeses described and claimed herein.

For purposes of describing the present invention, the term "particulate" shall be understood to include grated, shredded, comminuted and powdered food products, especially in the case of cheeses.

DETAILED DESCRIPTION OF THE INVENTION

The cellulose included in the products of the present invention are derived from a pulp having an ISO brightness of from about 80 to about 90. The ISO brightness is preferably from about 83 to about 89. Most preferably, however, the pulp has an ISO brightness of from about 85 to about 88.

The ISO pulp brightness determination is also referred to as an Elrepho Brightness of pulp test. This brightness determination method includes taking a sample of pulp and disintegrating it into a water slurry and recasting the pulp into uniform sheets using the TAPPI standard sheet mold. The handsheets are dried, cut, and the "percent brightness" is measured, for example, with an Elrepho photoelectric reflection photometer available from Carl Zeiss, Oberkochen, Germany. The pulp sample to be measured is placed at an opening at the bottom of an Ulbricht (integrating) sphere and is indirectly illuminated by completely diffuse light coming from two lamps which are inserted into the sphere. The light reflected from the sample passes through a blue filter (TAPPI 457) and is measured by a photocell. In a similar manner, light is also reflected from a standard white plate, located at a second opening on the sphere and measured by a second photocell. The difference in the current output from these two photocells is amplified and used to determine the brightness of the sample. Specular reflectance is eliminated by the use of a gloss trap. The blue filter is selected because cellulose normally has a yellowish color due to impurities. The reflectance in the blue region is most sensitive to bleaching changes, and the higher the reflectance in the blue part of the spectrum, the whiter a sheet will appear.

The scale of brightness used for this method is based on the reflectance of a perfect reflecting diffuser. For convenience, the standards used to calibrate the Elrepho are secondary paper tabs obtained monthly from The Institute of Paper Chemistry (IPC). Milk glass working standards which have been calibrated against the paper tabs are used for daily standardization of the meter. The results are then based on the method adopted by the International Standard Organization for Standardization (ISO).

The term "ISO brightness" is a term known and understood by those of skill in the art. It should be appreciated that other manners of identifying the pulp products used in the invention may be available. Equivalent pulp products having similar characteristics which are identified other than by ISO brightness are, of course, contemplated to be encompassed by the invention and appended claims.

By "cellulose", it is to be understood that the present invention contemplates natural carbohydrate polymers comprised of glucose units which are obtained from wood and non-wood sources. It is to be understood, however, that the cellulose used in the present invention can also include hemicelluloses, xylene hemicelluloses, mannan hemicelluloses, lignin, and the like. Furthermore, the cellulose can be in the form of particulates, granules, powders and the like. The present invention also contemplates including pulps per se in food products where such pulps can be sensorially undetected but yet provide bulking, fat mimetic or other useful properties.

Cellulose extraction and processing from wood pulp of fiber is well-known in the art. See, for example, U.S. Pat. Nos. 3,539,365 and 4,263,344, the contents of which are each incorporated by reference herein. For propose of the present invention, the cellulose is derived from pulp which has been rendered into an aqueous slurry or wet cake having a solids content ranging from about 5 to about 45% by weight. The cellulose wet cake may then be simply added to food products directly or spray dried to produce the desired cellulose granules, i.e., spheroids. In other aspects, the wet cake can be combined with additional processing ingredients if desired such as sodium carboxymethylcellulose, cellulose derivatives, stabilizers, preservatives, and the like. Depending on how the cellulose wet cake is treated, the particle size of these various resultant products may range from about 0.1 to about 10 microns and, in the non-colloidal aspects, from about 10 to about 100 microns. It is to be understood that these ranges may overlap somewhat and that particular sizes, shapes, lengths, etc. are within the level of skill of the art.

Celluloses having the desired ISO brightness are available from commercial sources such as Buckeye Cellulose Corp., Memphis, Tenn. One particularly preferred cellulose is derived from Buckeye's V-60 pulp having an ISO brightness of approximately 86–87.

In an alternative aspect of the invention, microcrystalline celluloses are included in the food products of the present invention. Microcrystalline cellulose is a processed cellulose and has been utilized extensively in the pharmaceutical industry. For example, commercially available microcrystalline celluloses include EMCOCEL® from Edward Mendell Co., Inc. and Avicel® from FMC Corp. Microcrystalline cellulose is prepared by partially depolymerizing cellulose obtained as a pulp from fibrous plant material with dilute mineral acid solutions. Following hydrolysis, the hydrocellulose is purified via filtration and the aqueous slurry is spray dried to form dry, white, odorless, tasteless, porous particles having a broad size distribution. Microcrystalline cellulose (MCC) is commercially available in several grades. For example, grated and shredded cheeses can include MCC with an average particle size ranging from 20 to 200 microns. Colloidal forms of MCC having particle sizes of less than about 0.2 microns are well suited for inclusion in liquid or semi-solid foods.

Microcrystalline cellulose, also known in the art as $\beta$-1-4-glucan, can be prepared to include other cellulosic materials such as carboxymethylcellulose or with various gums. See, for example, U.S. Pat. Nos. 3,539,365 and 4,263,344, the contents of which are each incorporated by reference herein. It is to be understood that the celluloses including microcrystalline cellulose and, any optionally included ingredient co-processed therewith typically in the form of an aqueous slurry, is dried and recovered as a powder. The recovered powder is typically obtained by spray drying the slurry in order to obtain the desired cellulose fibrous material of the particle size desired.

In the aspects of the invention where microcrystalline cellulose is used, it is to be understood that such products will also have an ISO brightness within the range described above. This is to be contrasted with the microcrystalline celluloses and other celluloses (i.e. powdered celluloses) routinely used in pharmaceuticals and food products which typically have an ISO brightness of from about 91 to 96. In order to achieve the desired ISO levels, a microcrystalline cellulose is obtained from a pulp or blend of pulps having the desired ISO level and rendered into microcrystalline cellulose using the techniques described above.

In yet another aspect of the invention, the cellulose is processed with one or more additional materials prior to being spray dried. In this regard, one or more materials such as carboxymethylcelluloses, polysaccharide gums such as guar, xanthan, carrageenan, alginates and the like as well as inorganic substances such as phosphates, sulfates and the like are included with the cellulose when it is in the form of a slurry prior to being spray dried.

In yet a further aspect of the invention, there are provided food products containing cellulose derived from a pulp having an ISO brightness of from about 80 to about 90; preferably from about 83 to about 89, and most preferably from about 85 to about 88. In this regard, food products such as sauces, fat-free food products, fat-reduced food products such as frozen desserts, viscous dressings, pourable dressings, nutritional products such as fortified powders, liquids or emulsions and the like, are provided. In this aspect of the invention, however, the cellulose, such as a microcrystalline cellulose, is admixed with the food ingredients in the form of an aqueous slurry rather than as a substantially dry particulate.

The celluloses of the present invention are also particularly well-suited for inclusion as the cellulose portion of fat mimetics and/or fat substitute bulking agents. For example, PCT International Publication No WO90/14017, the disclosure of which is incorporated by reference herein, describes a fat-like bulking agent formed by intimately admixing microcrystalline cellulose with guar gum in an aqueous medium and spray drying the mixture to form spheroidal aggregates. Optionally, additional food ingredients are co-processed with the MCC admixture to enhance taste or other desired properties. The MCC-based spheroids are preferably included in food products such as salad dressings or dairy products to provide a fat-like mouth-feel and consistency. As will be readily apparent to those of ordinary skill, the visual appeal of food products containing the cellulose-based fat mimetic is maximized by including celluloses derived from pulps having an ISO value which allows uniformity of color for the final product.

Generally, such food products will contain from about 0.25 to about 4% by weight of the dispersed cellulose, from about 50 to about 99% by weight water, from about 1 to about 35% by weight digestible carbohydrates, from about 0 to about 10% by weight protein, and from about 0 to about 10% by weight digestible triglycerides. A more complete description of the suitable products containing microcrystalline cellulose, and in particular, fat-free and fat-mimetic food products is found in U.S. Pat. No. 5,011,701, the contents of which are incorporated by reference herein.

Cellulose dispersions can be produced by providing an aqueous suspension of microcrystalline cellulose, for example, containing from about 90 to about 99% water and from about 1 to about 10% by weight microcrystalline cellulose derived from a pulp having an ISO brightness within the range described above. Preferably, the slurry will contain from about 5 to about 9% by weight of microcrystalline cellulose based on the weight of the aqueous dispersion. Furthermore, the microcrystalline cellulose particles included in the dispersion preferably have a mean particle size in the range of from about 5 to about 40 microns and preferably are in the range of from about 20 to about 30 microns.

The aqueous microcrystalline cellulose dispersion, can also be further processed to enhance its fat mimetic qualities. For example, the cellulose dispersion can be introduced into a high-shear mixer/homogenizer under high pressure, high shear zone to fragment the microcrystalline cellulose into cellulose fragments having a maximum dimension of less than about 1 micron and reagglomerating the sub-micron crystalline fragments under high shear conditions at a very small turbulence scale to produce porous micro-reticulated microcrystalline cellulose particles. The term "high pressure high shear zone" is meant to connote a shear zone operating at a driving pressure drop of at least 12,000 p.s.i., which is dissipated viscously to heat. Preferably, the microcrystalline cellulose is conducted through the high shear zone more than one time at a shear rate of at least about $5 \times 10^6$ seconds$^{-1}$ at a specific turbulent energy dissipation rate of at least about $8.5 \times 10^5$ ergs per cubic centimeter of the high shear zone. The exiting microcrystalline cellulose dispersion, sometimes referred to as "microreticulated", thus will have a desired viscosity suitable for inclusion in food products. Alternatively, the solids content of the dispersion can be adjusted via ultrafiltration, thin film evaporation or centrifugation procedures, if desired.

In a still further aspect of the invention, the thus attained microreticulated microcrystalline cellulose can be treated with an astringency control agent such as an ionic or neutral gum or mixture of gums in an amount of from about 5 to about 20 percent by weight of based on the total solids content of the microreticulated microcrystalline cellulose in aqueous dispersion. A non-limiting list of suitable ionic or neutral gums include xanthan, carboxymethylcellulose, carrageenan, alginates, locust bean gums, guar gums, and mixtures thereof. In this aspect, a low shear mixer such as a Hobart mixer or similar apparatus is used to combine the microcrystalline cellulose dispersion with the gum. The addition of the gum has the effect of improving mouth feel, texture, mitigating undesirable mouth feeling and sensations and also improve stability of the food product.

The microcrystalline cellulose dispersion can also be incorporated into frozen desserts as a fat substitute. For example, a low-calorie, low-fat or substantially fat-free frozen dessert can include from about 0 to about 2% edible fat, from about 1 to about 3% of the microcrystalline cellulose dispersion having the desired color characteristics described herein (as calculated on a dry weight basis), from about 2 to about 8% protein (dry basis), from about 10 to about 30% of a saccharide component containing one or more sugars, and from about 45 to about 85% water. Other stabilizers, gums and emulsifiers, flavorings agents and the like, can also be included if desired in amounts of up to 20% by weight.

Such frozen desserts can be prepared, for example, by thoroughly mixing and homogenizing, if necessary, water, protein, sweetening agents, fat if any, stabilizers and flavoring agents, subjecting the mixture to aeration, freezing and packaging the desserts in a conventional manner using standard techniques.

The microcrystalline cellulose dispersion can also be included in low oil or oil-free food dressings such as salad dressings, viscous and pourable dressings, and the like. These food compositions will generally include from about 0.25 to about 4% by weight and preferably from about 2 to 3% by weight of a cellulose dispersion (as calculated on a solids basis), from about 0 to about 7% fat or edible oil, and from about 50 to about 99% by weight of an aqueous fluid food dressing vehicle. Optional ingredients such as spices, seasonings and the like, can also be included therewith.

In accordance with conventional food dressing manufacturing techniques, the ingredients are combined by blending the ingredients using a vortex mixer, for example.

Also within this aspect of the invention are food products such as fat-free mayonnaise and similar products which are prepared in a manner similar to that described above with regard to salad dressings except that the food dressing vehicle may contain up to about 20% by weight of a "bodying" agent such as gums, starch, other hydrocolloids and mixtures thereof; low DE corn syrups and the like.

The present invention also includes substantially non-agglomerating particulate cheese products. In this aspect of the invention, particulate cheeses such as grated or shredded cheeses are combined with a cellulose derived from a pulp having an ISO brightness of from about 80 to about 90. Preferably, the cellulose is derived from a pulp or pulp blend having an ISO brightness of from about 83 to about 89 and most preferably from about 85 to about 88. The cellulose is present in an amount which is sufficient to substantially prevent agglomeration or caking of the cheese yet is not so great so as to detract from the organoleptic qualities of the final product.

The grated cheese, for example, may be any one of the commonly-found hard cheeses such as Parmesan, romano, Parmigiana, reggiano, lodigiano, lombardi, emiliano, veneto, baggozo, and the like. These cheeses differ in size, shape, fat content and moisture content but, for the purposes of the present invention, are included in the cheese products of the present invention. The moisture level of cured cheeses contemplated for use as grated cheeses is from about 15 to about 35% with amounts of from about 19 to about 24% being preferred. It will also be understood that the cheeses described above are listed for purposes of illustration only and those grated cheeses not specifically mentioned are also contemplated for use herein.

In order to provide the grated cheese, the hard cheese is usually first shredded and thereafter comminuted with suitable apparatus, such as a hammermill to provide the desired size cheese particles.

The shredded cheeses included in the present invention can be selected from any of the commonly known cheeses. A non-limiting list of suitable cheeses include cheddars, mozzarellas, Monterey Jack, colbys, Swiss, etc. and the like. The preparation of shredded cheeses is known in the art. For example, full moisture cheeses, i.e. cheeses containing moisture levels of up to about 30–35%, can be rendered into shreds by being continuously delivered to a multiple knife cheese shredder which comminutes the cheese into fragment shreds about an inch in length.

Regardless of whether the cheese included in the products of the present invention is grated, shredded, etc, the cheeses will tend to be primarily of a whitish, yellowish or orange-like shade. An important aspect of the invention, therefore is that the cellulose products mixed therewith to achieve the non-agglomerating effect have a color which substantially matches that of the selected cheese.

The cellulose included in the cheese products of the present invention, the cellulose will be present in an amount of from about 0.01 to about 5% based on the weight of the cheese portion of the final product. In preferred aspects, the cellulose is present in amounts of from about 0.05 to about 2%; and in most preferred aspects of the invention, the cellulose is present in an amount of from about 0.1 to about 1.5% by weight.

Since grated cheese particles are generally spheroidal in shape, it is preferred that the cellulose also be in the form of spheroids or generally spheriodal particles. In this regard, the non-agglomerating effect of the cellulose is achieved when the cellulose has an average diameter of from 10 to about 1000 microns, and more preferably having a diameter of from about 40 to about 400 microns.

In the case of shredded cheeses, the cellulose can also be in the form of a spheroid and within the diameter ranges set forth above, although the larger surface areas of shreddings affords the artisan with the capability of including other shapes and sizes so long as the organoleptic and visual characteristics of the cheese are not substantially effected.

As a further assurance of avoiding agglomeration of the cheese products of the present invention, the cellulose product included in the present invention should have a moisture content of from about 0.5 to about 10 % by wt., preferably from about 1 to about 8 and most preferably from about 2.5 to about 6 % by wt.

The particulate cheese products of the present invention can also include additional materials such as preservatives, anti-caking agents, flavors, spices and related materials known to those of ordinary skill in the art as well as mixtures thereof. For example, suitable anti-caking agents include silicon dioxide, calcium silicate, sodium silico aluminate, disodium phosphate, and mixtures thereof.

In a further aspect of the invention, there is provided a method of preparing a substantially non-agglomerating particulate cheese product. This aspect of the invention includes blending a cellulose described above, that is, a cellulose derived from a pulp having an ISO brightness of from at least about 80 to about 90, with a grated or shredded cheese until a homogeneous mixture is obtained. The combining of the ingredients is preferably carried out using dry blending of the material so that the cellulose particles are substantially dispersed throughout the cheese particles. As an alternative, if the cheese particles are to be dried prior to final packaging, the cellulose can be distributed throughout the cheese particles during air drying. In the case of grated cheeses, the cellulose and cheese can also be commingled with the cheese in shredded form before undergoing final comminution into its final size such by a hammer mill or other suitable device. As the mixture undergoes disintegration, the cellulose becomes thoroughly dispersed with the cheese. Alternatively, the cellulose can be sprinkled on the cheeses and the mixture tossed prior to packaging.

The amount of cellulose admixed with the cheese particles is an amount which is sufficient to substantially prevent agglomeration of the particulate cheese product. In this regard, as commented above, the amounts of cellulose combined with the particulate cheese will range from about 0.01 to about 5% by weight with preferred amounts being from 0.05 to about 2% and most preferred amounts being from about 0.1 to about 1.5%.

It is to be understood that the amount of cellulose included is an amount which is sensorially undetected, particularly with regard to sight and mouth feel so that the consumer sees a substantially uniform color in the particulate final product and enjoys an organoleptically pleasing product. Thus, in one aspect of the method described herein, the artisan matches the color of the cellulose to the particulate cheese product included in the final product prior to the blending.

In a still further aspect of the invention there is provided a method of matching the color of a cellulose with the color of a food product. The method includes blending two or more pulps to obtain an ISO brightness which substantially matches the color of the food product and rendering the blended pulp into cellulose. Although pulps will differ due to the variances in sources and tree species, the pulps can be selected from wood and non-wood pulps include those obtained from hemlocks, spruces, pines, eucalyptus, cotton, cotton fiber, cotton linter, sugar beet, etc. Buckeye Cellulose Corporation, for example sells several different grades of memphis cotton linter pulps, foley wood pulps and the like. This list is merely illustrative and not to be construed as limiting the pulp sources described herein. Two or more of the these pulps and others can be mixed in order to provide a cellulose having desired color qualities. By deriving cellulosic materials from such pulps, the artisan is able to provide not only aesthetically pleasing food adjuncts, but also is able to provide celluloses which offer substantial cost savings over conventional MCC-based food additives which are derived from celluloses having much higher ISO values.

While Applicants do not intend to be bound by theory, it is believed that the inter-dispersing of the cellulose among the cheese particles achieves at least three effects. First, the anti-caking and non-agglomerating action of the cellulose is achieved. Second, the visual sensation of having a uniformly-appearing product asses consumer acceptance. Third, the cellulose used in the food products of the present invention do not contribute to the taste of the food product as a whole.

In a still further aspect of the present invention, there are provided oral solid dosage forms containing the cellulose products described herein. The dosage forms may be in the form of a compressed tablet, capsule, sachet, etc. Within this aspect of the invention, the solid dosage form can include one or more pharmaceutically acceptable active ingredients or even confectionery ingredients such as those found in pressed mints. The cellulose products afford the artisan with the advantages of lower cost cellulose diluents and also avoid the use of microcrystalline celluloses which have undergone bleaching or other treatments which can have an environmentally harmful effect.

EXAMPLES

The following examples illustrate various aspects of the present invention. They are not to be construed to limit the claims in any manner whatsoever. It will be readily apparent to one skilled in the art that the cellulose products of the present invention will find a wide range of uses in a wide variety of food products, pharmaceuticals, such as tablets, powders or sachets, nutritional products and the like. Such embodiments of the invention are to be encompassed by the appended claims.

Example 1

In this example, about 6.2 kg. of hydrolyzed, washed and filtered cellulose wetcake derived from Buckeye V-60 raw pulp (Buckeye Cellulose Corp.) ISO 86-87 was combined with 5.2 kg of water in a mix tank to form a slurry containing about 15% solids. The pH was adjusted to about neutral with about 3 ml of ammonium hydroxide. The slurry was allowed to mix and become a homogeneous mixture. The slurry was then spray dried using a Niro Production Minor (Niro, Columbia, Md.), inlet temperature: 215° C., outlet temperature: 125° C., atomizer wheel speed: 22,300 rpm to provide cellulose particles having an average particle size of about 40 to about 60 microns.

Example 2

In this example, the process of Example 1 is repeated except that the resulting spray-dried cellulose particles are re-dispersed in distilled water with sufficient agitation to form a substantially homogenous dispersion.

Example 3

Full moisture Parmesan cheese having a moisture content of from about 30 to about 32% is continuously delivered by a moving ram into a 15-knife cheese shredder (Murray Machinery) which comminutes the cheese into fragment shreds ranging up to 1 inch in length. The Parmesan shreds are then delivered to a hammer mill disintegrator (Rietz Co.). At the same time, the shredded cheese is being conveyed to the hammer mill, the cellulose particles obtained as a result of Example 1 derived from V-60 pulp (Buckeye Cellulose Corp.) is added through a volumetric filler into the shredded cheese just ahead of the hammer mill disintegrator. The volumetric ratio of additives is designed to yield a 0.5% level of cellulose by weight in the dried grated Parmesan at about 22% moisture.

The hammer mill disintegrator comminutes the Parmesan cheese shreds in conjunction with the cellulose (ISO brightness approximately 86-87) to provide a homogeneous blend of the grated cheese particles and cellulose particles. The resulting cheese has a particle size ranging from about 0.5 mm to about 1.7 mm in diameter. At this point in the process, the moisture level of the Parmesan is about 27 to about 29% by weight and pH is about 5.45. The grated Parmesan cheese-cellulose blend is then directed to a fluid bed dryer (Carrier, Inc.) and dried until the finished grated Parmesan cheese is determined to have about a 22% moisture content. The dried grated cheese product is thereafter placed into containers ready for sale to consumers and is found to be substantially non-agglomerating and flows readily from containers. In addition, the final product was also found to be pleasing to the eye and without detectable amounts of contrasting specks of cellulose.

After two months storage under refrigerated conditions (about 45° F.), samples of the grated cheese product are evaluated for degree of caking within a container and flowability out of the container. After two months, very minimal caking is observed and flowability of the Parmesan out of the container is determined to be very good. This is to be contrasted with higher moisture grated Parmesan cheese, i.e., greater than 19% moisture without anti-caking ingredients, typically experience caking under refrigeration conditions and are lumpy when dispensed from containers. It is known that caking generally intensifies with increasing moisture levels above 19%.

Examples 4

Full moisture cheddar cheese having a moisture content of between about 30 to about 32% is continuously delivered by a moving ram into a 15-knife cheese shredder (Murray Machinery) which comminutes the cheese into fragment shreds ranging up to 1 inch in length. The shredded cheese is thereafter combined with the cellulose particles prepared in accordance with the procedure of Example 1 except that the cellulose is derived from pulp having an ISO brightness of about 83. This cellulose is selected on the basis of its substantial similarity in color to that of the particular cheddar cheese. The cellulose and cheddar cheese shreds are then intimately combined by physical admixture so that the cellulose is present in an amount of about 0.5% by weight. The cheese product is then packaged into 8 oz. resealable plastic containers.

The cheese product mixture is found to have very minimal caking or clumping and the shreds are easily dispersed upon tossing.

Example 5

A substantially fat-free buttermilk-type dressing was prepared utilizing the cellulose dispersion of Example 2. The pourable dressing was prepared according to the following formula:

| INGREDIENTS | % BY WEIGHT |
| --- | --- |
| Water | 47.82 |
| Cultured low-fat buttermilk | 20.00 |
| 25 DE corn syrup | 15.00 |
| Cellulose particles of Ex. 2 | 2.70 |
| Blended margarine oil | 2.50 |
| Vinegar | 2.50 |
| Sucrose | 2.00 |
| Salt | 1.40 |
| Xanthan gum | 0.50 |
| Phosphoric acid | 0.79 |
| Flavors and spices | q.s. |
| Total | 100 |

The cellulose dispersion is placed in a high shear Breddo pump vortex mixer. The xanthan gum and sugar are blended together and slowly added to the cellulose dispersion under vortex mixing conditions and mixed for several minutes until a homogeneous mixture is obtained. The low DE corn syrup in combination with the other ingredients is subsequently added to the blend under vortex shear conditions. Separately, a partially hydrogenated soybean oil having a melting point of about 100°–105° F. and an iodine value of about 92.5–90 is melted and added last to evenly disperse the oil without emulsifying the oil. The dressing is found to have pleasing organoleptic characteristics and is substantially uniform in color.

Example 6

In this example, a substantially fat-free French-type dressing is prepared according to the following formula:

| INGREDIENTS | % BY WEIGHT |
| --- | --- |
| Water | 2.95 |
| 25 DE corn syrup | 20.00 |
| Sugar | 10.50 |
| Vinegar | 6.00 |
| Partially hydrogenated soybean oil | 2.60 |
| Cellulose particles of Ex. 2 | 2.00 |
| Salt | 1.85 |
| Xanthan gum | 0.55 |
| Stabilizers and acidifiers | 0.34 |
| Flavors and spices | q.s. |
| Total | 100 |

The procedure of the previous example was repeated in order to provide a French-type dressing which is also found to have pleasing organoleptic characteristics.

While there have been described what are presently believed to be the preferred embodiments of the invention, those skilled in the art will realize that changes and modification may be made thereto without departing from the spirit of the invention. It is intended to claim all such changes and modifications that fall within the true scope of the invention.

What is claimed is:

1. A substantially non-agglomerating cheese product in shredded, grated or particulated form, comprising:
   a) an edible cheese material which is shredded, grated or particulate; and
   b) a cellulose derived from a pulp selected from the group consisting of wood pulps, cotton pulps and eucalyptus pulps having an ISO brightness from about 80 to about 90, said cellulose being present in an amount which is sufficient to substantially prevent agglomeration of said cheese material.

2. The cheese product of claim 1, wherein said pulp has an ISO brightness of from about 83 to about 89.

3. The cheese product of claim 2, wherein said pulp has an ISO brightness of from about 85 to about 88.

4. The cheese product of claim 1, wherein said cellulose is selected from the group consisting of microcrystalline cellulose, powdered cellulose and mixtures thereof.

5. The cheese product of claim 1, wherein said cellulose is present in an amount of from about 0.01 to about 5% based on the weight of said cheese product.

6. The cheese product of claim 5, wherein said cellulose is present in an amount of from about 0.05 to about 2% based on the weight of said cheese product.

7. The cheese product of claim 6, wherein said cellulose is present in an amount of from about 0.1 to about 1.5% based on the weight of said particulate cheese product.

8. The particulate cheese product of claim 16, wherein said cellulose comprises generally spheroidal particles having an average diameter from about 40 to about 400 microns.

9. The cheese product of claim 1, wherein said wood pulp is selected from the group consisting of hard wood pulps, soft wood pulps and mixtures thereof.

10. A method of preparing a substantially non-agglomerating solid cheese product which is shredded, grated or particulate, comprising:
   (a) obtaining an edible cheese material which is shredded, grated or particulate which has an ISO brightness from about 80 to about 90;
   (b) obtaining an anti-caking agent consisting of cellulose derived from a pulp selected from the group consisting of wood pulps, cotton pulps and eucalyptus pulps having an ISO brightness from about 80 to about 90 which substantially matches the ISO brightness of said cheese material; and
   (c) blending said cellulose with said cheese material in an amount sufficient to substantially prevent agglomeration of discrete portions of said cheese material, to provide said cheese product.

11. The method of claim 10, further comprising matching the color of said cellulose to said particulate cheese product prior blending.

12. The method of claim 11, wherein said pulp has an ISO brightness of from about 83 to about 89.

13. The method of claim 12, wherein said pulp has an ISO brightness of from about 85 to about 88.

14. A method of preparing a solid cheese product which is shredded, grated or particulate, comprising:
   (a) obtaining an edible cheese material which is shredded, grated or particulate which has an ISO brightness from about 80 to about 90;
   (b) blending two or more pulps where one or more pulp is selected from the group consisting of wood pulps, cotton pulps and eucalyptus pulps to form a pulp blend having an ISO brightness from about 80 to about 90, where the color of said pulp blend substantially matches the color of said cheese material;
   (c) deriving a plurality of cellulose particles having a uniform color from said pulp blend; and
   (d) blending said cheese material and said cellulose particles, to provide a cheese product having substantially uniform color which is substantially free from agglomeration.

15. The method of claim 14, wherein said pulp blend has an ISO brightness of from about 80 to about 90.

16. The method of claim 5, wherein said pulp blend has an ISO brightness of from about 83 to about 89.

17. The method of claim 16, wherein said pulp blend has an ISO brightness of from about 85 to about 88.

18. The method of claim 14 wherein the cellulose is free from added colorants.

* * * * *